United States Patent [19]
Calí

[11] Patent Number: 4,748,976
[45] Date of Patent: Jun. 7, 1988

[54] ANATOMICAL DRESSINGS FOR COSMETIC TREATMENTS

[76] Inventor: Romano Calí, Corso Itali, 72, Catania, Italy, 95129

[21] Appl. No.: 870,934

[22] Filed: Jun. 5, 1986

[30] Foreign Application Priority Data

Sep. 11, 1985 [IT] Italy .............................. 36156/85[U]

[51] Int. Cl.$^4$ .............................................. A61L 15/00
[52] U.S. Cl. ..................................... 128/156; 132/88.5
[58] Field of Search .................... 128/156, 5; 132/88.5, 132/88.7, 83

[56] References Cited

U.S. PATENT DOCUMENTS

| | | | |
|---|---|---|---|
| 273,410 | 3/1883 | Wadleigh | 604/304 |
| 1,532,238 | 4/1925 | Farrell | 132/88.5 |
| 1,850,540 | 3/1932 | Erickson | 132/88.5 |
| 2,527,947 | 10/1950 | Loos | 132/88.5 |
| 2,671,898 | 3/1954 | Wade | 128/132 R |
| 3,367,329 | 2/1968 | Dibelius | 128/132 R |
| 3,478,739 | 11/1969 | Librande | 128/132 R |
| 3,596,657 | 8/1971 | Eidus | 604/304 |

OTHER PUBLICATIONS

Sagarin, Cosmetics–Science and Technology, 1957, pp. 258 and 848.

Primary Examiner—Gregory E. McNeill
Attorney, Agent, or Firm—Thomas R. Vigil

[57] ABSTRACT

The anatomical dressings disclosed provide a support material of close-textured, 100% cotton fabric which can be impregnated with cosmetic preparations held in an oil or a grease medium. The single dressing is cut to match the contours of that part of the anatomy to be treated, and when applied, remains fast by virtue of surface adhesion for whatever length of time is suitable in the case of the particular treatment.

20 Claims, 1 Drawing Sheet

FIG. 6
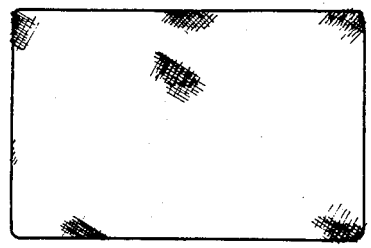
FIG. 4
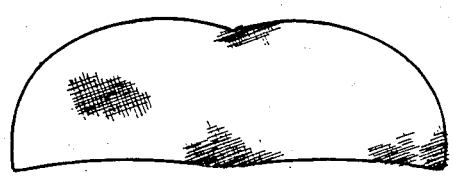
FIG. 2
FIG. 1
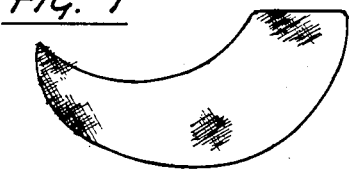
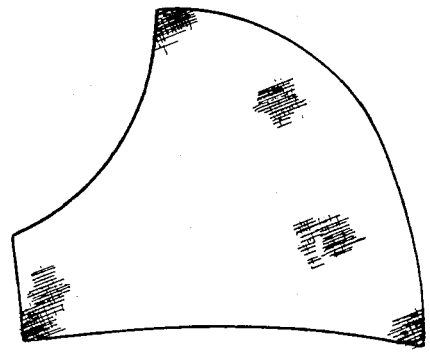
FIG. 3
FIG. 5
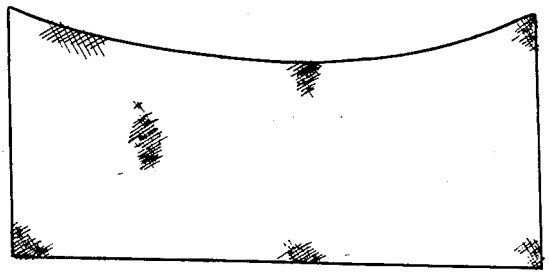

ANATOMICAL DRESSINGS FOR COSMETIC TREATMENTS

BACKGROUND OF THE INVENTION

The invention relates to a cosmetic treatment of defects manifested by the skin of the face and body, utilizing products applied in combination and in conjunction with one another.

All of the cosmetic treatments currently in use involve the application of a given preparation, generally emulsions of oil in water or water in oil, direct to the skin; whatever the method and system employed in such application, the need exists for dispensing a given amount of the preparation locally and distributing it over the area to be treated, not infrequently with the aid of support materials (e.g. swabs, bandages &c.) which may occasion unwarranted removal of a part of the preparation, and in consequence, an incorrect distribution other than as intended, not to mention other foreseeable drawbacks.

The object of the invention disclosed is that of creating a cosmetic treatment featuring embodiment of a support material for cosmetic substances and compounds that will adhere correctly and for a given length of time to the surfaces of the face and body requiring treatment.

A further object of the invention is that of ensuring a correct and balanced distribution of the cosmetic preparation over the area of skin requiring treatment, and a persistent action enabling deeper and more gradual penetration into the skin, hence increased absorption by the tissues.

An additional object of the invention is that of exploiting the support to obtain a mask effect aimed at keeping dehydration of the skin down to a minimum.

SUMMARY OF THE INVENTION

The stated objects, and others besides, are realized with anatomical dressings according to the invention the essential feature of which, generally cnsidered, is that of providing a support material consisting in a close-textured pure cotton fabric, soaked in or impregnated with a cosmetic preparation held in an oil or grease medium, which is cut out to match the contours of that part of the anatomy to be treated and applied thereto, remaining fast through surface adhesion for a given length of time.

Dressings thus cut from close-textured pure cotton fabric are electrically neutral, chemically inactive, and anatomically shaped,and are soaked in or impregnated with special skin care preparations in order to enable their application to different parts of the face and body, thereby limiting and concentrating the effect of active substances in the preparation, to and on the area requiring treatment.

BRIEF DESCRIPTION OF THE DRAWINGS

Preferred shapes of the anatomical dressings for cosmetic treatments as described herein are illustrated, by way of example, in the accompanying drawings, in which:

FIG. 1 is a periocular dressing for application over the lower eyelid and crow's feet, so-called, extending from the inner corner of the orbit and the root of the nose around to the temporofrontal hairline;

FIG. 2 is a dressing for application to 'bags' under the eyes, reflecting the exact anatomy of the lower eyelid, which is the source of the edema that produces swelling;

FIG. 3 is a facial dressing the outline of which departs from the lateral insertion of the nose, follows the nasolabial fold down toward the corner of the mouth, continues around the mandibular contour of the face, passes beneath the lower eyelid and rejoins the nose at its uppermost insertion;

FIG. 4 is a forehead dressing which borders at bottom with the eyebrow line, and exhibits a side and top outline of elongated half-oval shape corresponding to the frontoparietal hairline;

FIG. 5 is a neck dressing shaped in such a way that each side borders with the sternocleidomastoid line, the bottom edge coincides with the clavicular insertion, and the top edge follows the contour of the mandibles; a dressing for application to the lower part of the breast would be of substantially half-moon shape;

FIG. 6 illustrates a dressing of substantially quadrangular shape for the abdomen and hips, the effective dimensions of which will vary according to the part of the anatomy to be covered.

DESCRIPTION OF THE PREFERRED EMBODIMENTS

Dressings as shaped in the drawings are soaked in or impregnated with any such cosmetic substance as may be permitted by law, the medium of which will generally be oil (lanolin and its derivatives) or grease (vaseline and its derivatives). An anatomical dressing according to the invention is classifiable, on the basis of the preparation impregnated and the active substances it contains, as serving: for the treatent of facial wrinkles, for the treatment of acne; for soothing inflammation (herbal compounds); for moisturizing, nourishing, revitalizing, restoring, firming-up and invigorating the skin; for the treatment of bags under the eyes; for firming-up the breasts; or for the treatment of cellulitis.

Following application, dressings will adhere gently to that part of the anatomy requiring attention; moreover, correct and effective treatment will be obtained where such adhesion is maintained for a given length of time, which is dependent on the particular treatment.

Anatomical dressings according to the invention provide the following basic advantages over the types of treatment in current use:

a greater quantity of the cosmetic preparation brought into contact with that part of the anatomy being treated;

persistent action produced by the preparation as a result of its being dispensed directly onto the skin by the dressing;

greater penetration of the preparation through the skin and into the connective tissue, by virtue of the medium adopted, and of the quantity of the preparation applied and its persistent action on the skin;

a dehydration-inhibiting mask effect produced by application of the impregnated dressing to the area being treated;

more immediate and readily discernable results in care of the skin.

What is claimed:

1. Anatomical dressings for cosmetic treatments of a skin surface, consisting in a sheet of close-textured pure cotton fabric, soaked in or impregnated with a cosmetic preparation held in an oil or grease medium, a portion of which is cut from the sheet to match the contours of that part of the anatomy to be treated and applied thereto, remaining attached to the skin through surface adhesion for a given length of time.

2. Anatomical dressings for cosmetic treatments as in claim 1, wherein the medium in which the cosmetic preparation is held is a lanolin compound or derivative thereof.

3. Anatomical dressings for cosmetic treatments as in claim 1, wherein the medium in which the cosmetic preparation is held is a vaseline compound or derivative thereof.

4. Anatomical dressings for cosmetic treatments as in claim 1, wherein the fabric is cut to permit a periocular application whereby the dressing matches the shape of the skin, from along a lower eyelid, extending from the inner corner of the orbit and the root of the nose to the temporofrontal hairline.

5. Anatomical dressings for cosmetic treatments as in claim 1, wherein the fabric is cut to permit application to the lower eyelid skin only, inasmuch as the dressing matches the shape of that part of the orbit.

6. Anatomical dressings for cosmetic treatments as in claim 1, wherein the fabric is cut to permit a facial application whereby the outline of the dressing departs from the lateral insertion of the nose, follows the nasolabial fold downward, closely skirting the corner of the mouth, continues around the mandibular contour of the face, passes beneath the lower eyelid and rejoins the nose at its uppermost insertion.

7. Anatomical dressings for cosmetic treatments as in claim 1, wherein the fabric is cut to permit application to the forehead, with the dressing bordering at a bottom edge on the eyebrow line and exhibiting a side and top outline of elongated half-oval shape corresponding to the frontoparietal hairline.

8. Anatomical dressings for cosmetic treatments as in claim 1, wherein the fabric is cut to permit application to the neck, with the dressing shaped such that each side borders with the sternocleidomastoid line, the bottom edge coincides with the clavicular insertion, and the top edge follows the contour of the mandibles.

9. Anatomical dressings for cosmetic treatments as in claim 1, wherein the fabric is cut to permit application to the lower part of the skin of the breast, with the dressing matched to the contours of that lower skin area of the breast which is to be covered.

10. Anatomical dressings for cosmetic treatments as in claim 1, wherein the fabric is cut substantially to quadrangular shape to permit application to the abdomen and hips, and the dressing exhibits dimensions commensurate with the size of that skin area of the anatomy which is to be covered.

11. An anatomical dressing for applying medicaments to an area of skin comprising:
a medicament;
a lubricative medium intermixed with said medicament; and
a sheet of close-textured substantially pure cotton fabric shaped by cutting to match the contours of the portion of the anatomy to be treated, said intermixture of said medicament and said medium impregnating said fabric, said impregnated fabric being applied to the skin in the area to be treated adhering by surface adhesion of the medium to the skin for a predetermined time interval.

12. The anatomical dressings of claim 11 for application of medicaments to an area of skin wherein the medium in which the medicament is held is a lanolin compound or derivative thereof.

13. The anatomical dressings of claim 11 for application of medicaments to an area of skin wherein the medium in which the medicament is held is a vaseline compound or derivative thereof.

14. The anatomical dressings of claim 11 for application of medicaments to an area of skin wherein the sheet of fabric is specifically shaped by cutting the fabric to permit a periocular application whereby the dressing matches the shape of the skin from along a lower eyelid, extending from the inner corner of the orbit and the root of the nose to the temporofrontal hairline.

15. The anatomical dressings of claim 11 for application of medicaments to an area of skin wherein the sheet of fabric has been specifically shaped by cutting the sheet of fabric to permit application to the skin of the lower eyelid only.

16. The anatomical dressings of claim 11 for application of medicaments to an area of skin wherein the fabric has been specifically shaped by cutting the fabric to permit a facial application whereby the outline of the shape of the dressing extends from the lateral insertion of the nose, follows the nasolabial fold downward, closely skirting the corner of the mouth, continues around the mandibular contour of the face, passes beneath the lower eyelid and rejoins the nose at its uppermost insertion.

17. The anatomical dressings of claim 11 for application of medicaments to an area of skin wherein the sheet of fabric has been specifically shaped by cutting the fabric to permit application to the forehead, with a lower dressing edge bordering the eyebrow line and the dressing exhibiting a side and top outline of elongated half-oval shape corresponding to the frontoparietal hairline.

18. The anatomical dressing of claim 11 for application of medicaments to an area of skin wherein the sheet of fabric has been specifically shaped by cutting the sheet of fabric to permit application to the neck, with the dressing shaped such that each side borders the sternocleidomastoid line, a bottom edge coincides with the clavicular insertion, and a top edge follows the contour of the mandible.

19. The anatomical dressings of claim 11 for application of medicaments to an area of skin wherein the sheet of fabric has been specifically shaped by cutting the sheet of fabric to permit application to the skin of the lower part or underside of the breast, the shape of the dressing matching the contour of that skin area of the breast which is to be covered.

20. The anatomical dressings of claim 11 for application of medicaments to an area of skin wherein the fabric has been specifically shaped by cutting the fabric substantially to a quadrangular shape to permit application to the skin of the abdomen and hips, the dressing exhibiting dimensions equal to the size of that area of the skin to be covered.

* * * * *